US00PP35098P2

(12) United States Plant Patent
Flore

(10) Patent No.: US PP35,098 P2
(45) Date of Patent: Apr. 11, 2023

(54) ***PHALAENOPSIS* PLANT NAMED 'MI02648'**

(50) Latin Name: *Phalaenopsis hybrida*
Varietal Denomination: MI02648

(71) Applicant: MICROFLOR N.V., Lochristi (BE)

(72) Inventor: Febe Flore, Lochristi (BE)

(73) Assignee: MICROFLOR N.V., Lochristi (BE)

( * ) Notice: Subject to any disclaimer, the term of this patent is extended or adjusted under 35 U.S.C. 154(b) by 0 days.

(21) Appl. No.: 17/827,945

(22) Filed: May 30, 2022

(51) Int. Cl.
*A01H 5/02* (2018.01)
*A01H 6/62* (2018.01)

(52) U.S. Cl.
USPC ..... Plt./311

(58) Field of Classification Search
USPC ..... Plt./311
See application file for complete search history.

(56) References Cited

PUBLICATIONS https://online.plantvarieties.eu/publicSearch?denomination=MI02648;CVPO Register—CPVO Application Consulation; version 4.2.4; retrieved on Jul. 8, 2022, citationfor 'MI026481'.*

* cited by examiner

*Primary Examiner* — Susan McCormick Ewoldt
(74) *Attorney, Agent, or Firm* — C. Anne Whealy

(57) ABSTRACT

A new and distinct cultivar of *Phalaenopsis* plant named 'MI02648', characterized by its upright plant habit; vigorous growth habit and rapid growth rate; strong and flexible flowering stems; compact and semi-erect leaves; freely flowering habit with typically two inflorescences per plant, each inflorescence with numerous flowers; bright yellow-colored flowers with reddish orange-colored stripes that resist fading; and good postproduction longevity.

1 Drawing Sheet

Figure 1:
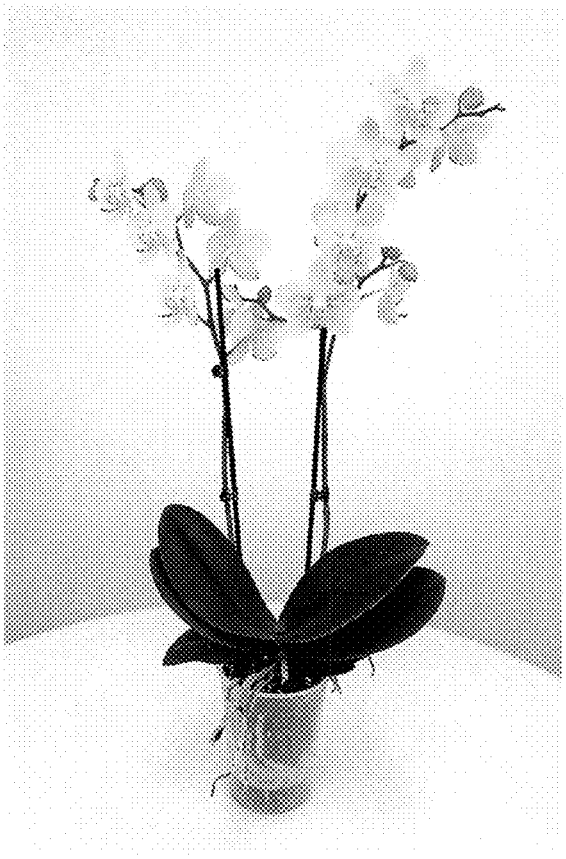

Botanical designation: *Phalaenopsis hybrida.*
Cultivar denomination: 'MI02648'.

BACKGROUND OF THE INVENTION

The present invention relates to a new and distinct cultivar of *Phalaenopsis* plant, botanically known as *Phalaenopsis hybrida*, and hereinafter referred to by the name 'MI02648'.

The new *Phalaenopsis* plant is a product of a planned breeding program conducted by the Inventor in Lochristi, Belgium. The objective of the breeding program is to develop new freely flowering *Phalaenopsis* plants with good leaf shape and relatively large flowers with unique and attractive flower coloration.

The new *Phalaenopsis* plant originated from a cross-pollination by the Inventor in September, 2016 in Lochristi, Belgium of a proprietary selection of *Phalaenopsis hybrida* identified as code number PHM00322, not patented, as the female, or seed, parent with a proprietary selection of *Phalaenopsis hybrida* identified as code number PH02885, not patented, as the male, or pollen, parent. The new *Phalaenopsis* plant was discovered and selected by the Inventor as a single flowering plant from within the progeny of the stated cross-pollination grown in a controlled greenhouse environment in Lochristi, Belgium in May, 2019.

Asexual reproduction of the new *Phalaenopsis* plant by in vitro meristem propagation in a controlled environment in Lochristi, Belgium since August, 2020 has shown that the unique features of this new *Phalaenopsis* plant are stable and reproduced true to type in successive generations.

SUMMARY OF THE INVENTION

Plants of the new *Phalaenopsis* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'M102648'. These characteristics in combination distinguish 'M102648' as a new and distinct *Phalaenopsis* plant:

1. Upright plant habit.
2. Vigorous growth habit and rapid growth rate.
3. Strong and flexible flowering stems.
4. Compact and semi-erect leaves.
5. Freely flowering habit with typically two inflorescences per plant, each inflorescence with numerous flowers.
6. Bright yellow-colored flowers with reddish orange-colored stripes that resist fading.
7. Good postproduction longevity.

Plants of the new *Phalaenopsis* can be compared to plants of the female parent selection. Plants of the new *Phalaenopsis* differ primarily from plants of the female parent selection in the following characteristics:

1. Plants of the new *Phalaenopsis* flower two weeks earlier than plants of the female parent selection.
2. Plants of the new *Phalaenopsis* produce twice as many flowers per inflorescence as plants of the female parent selection.
3. Flowers of plants of the new *Phalaenopsis* are bright yellow in color with reddish orange-colored stripes whereas flowers of plants of the female parent selection are yellow in color with greyed orange-colored spots.

Plants of the new *Phalaenopsis* can be compared to plants of the male parent selection. Plants of the new *Phalaenopsis* differ primarily from plants of the male parent selection in the following characteristics:

1. Flower buds of plants of the new *Phalaenopsis* are solid yellowish green in color whereas flower buds of plants of the male parent selection are yellowish green in color with violet-colored stripes.
2. Central lobe of the labellum of plants of the new *Phalaenopsis* are trullate in shape whereas central lobe of the labellum of plants of the male parent selection are triangular in shape.
3. Flowers of plants of the new *Phalaenopsis* are bright yellow in color with reddish orange-colored stripes whereas flowers of plants of the male parent selection are white in color with violet-colored stripes.

Plants of the new *Phalaenopsis* can be compared to plants of *Phalaenopsis hybrida* 'Fuller's Secret', not patented. In side-by-side comparisons, plants of the new *Phalaenopsis* differ primarily from plants of 'Fuller's Secret' in the following characteristics:

1. Plants of the new *Phalaenopsis* have slightly smaller flowers than plants of 'Fuller's Secret'.
2. Flowers of plants of the new *Phalaenopsis* are bright yellow in color with reddish orange-colored stripes whereas flowers of plants of 'Fuller's Sunset' are yellow in color without stripes.

BRIEF DESCRIPTION OF THE PHOTOGRAPHS

The accompanying photographs illustrate the overall appearance of the new *Phalaenopsis* plant showing the colors as true as it is reasonably possible to obtain in colored reproductions of this type. Colors in the photographs may differ slightly from the color values cited in the detailed botanical description which accurately describe the colors of the new *Phalaenopsis* plant.

The photograph at the top of the sheet (FIG. 1) is a side perspective view of a typical flowering plant of 'MI02648' grown in a container.

Figure 2:
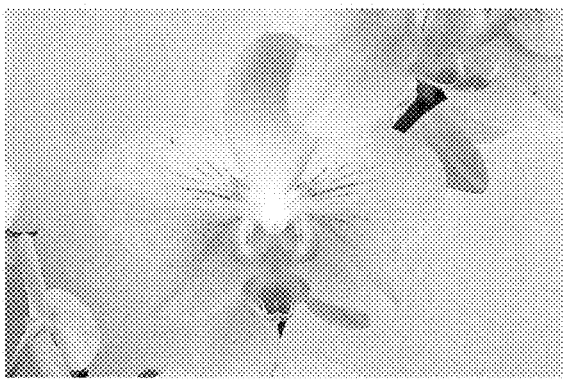

The photograph at the bottom of the sheet (FIG. 2) is a close-up view of typical flowers of 'MI02648'.

DETAILED BOTANICAL DESCRIPTION

The aforementioned photographs and following observations and measurements describe plants grown during the winter in 12-cm containers in a glass-covered greenhouse in Lochristi, Belgium and under cultural practices typically used in commercial *Phalaenopsis* production. During the production of the plants, day and night temperatures ranged from 18° C. to 29° C. and light levels ranged from 150 Watt/m$^2$ to 375 Watt/m$^2$. Plants were 69 weeks old when the photographs and description were taken. In the following description, color references are made to The Royal Horticultural Society Colour Chart, 2015 Edition, except where general terms of ordinary dictionary significance are used.

Botanical classification: *Phalaenopsis hybrida* 'MI02648'.

Parentage:

*Female parent*.—Proprietary selection of *Phalaenopsis hybrida* identified as code number PHM00322, not patented.

*Male parent*.—Proprietary selection of *Phalaenopsis hybrida* identified as code number PH02885, not patented.

Propagation:

*Type*.—By in vitro meristem propagation.

*Time to initiate roots, summer*.—About nine to ten weeks at temperatures about 26° C.

*Time to initiate roots, winter*.—About ten to eleven weeks at temperatures about 26° C.

*Time to produce a rooted young plant, summer*.—About 140 to 160 days at temperatures about 26° C.

*Time to produce a rooted young plant, winter*.—About 150 to 180 days at temperatures about 26° C.

*Root description*.—Thick, fleshy; typically grey green in color; actual color of the roots is dependent on substrate composition, water quality, fertilizer, substrate temperature and age of roots.

*Rooting habit*.—Small amount of branching; sparse.

Plant description:

*Plant form and growth habit*.—Herbaceous epiphyte; upright plant habit with typically two inflorescences per plant, each inflorescence with numerous flowers; monopodial; vigorous growth habit and rapid growth rate.

*Plant height, substrate level to top of foliar plane*.—About 15 cm.

*Plant height, substrate level to top of inflorescences*.—About 55 cm.

*Plant diameter or spread*.—About 42 cm.

Leaf description:

*Arrangement and quantity*.—Distichous, simple; sessile; about eight leaves per plant.

*Length*.—About 17 cm.

*Width*.—About 8.5 cm.

*Aspect*.—Semi-erect.

*Shape*.—Elliptic to slightly oblanceolate.

*Apex*.—Unequal obtuse.

*Base*.—Sheathing.

*Margin*.—Entire.

*Texture and luster, upper and lower surfaces*.—Smooth, glabrous; moderately glossy.

*Venation pattern*.—Camptodromous.

*Color*.—When opening and fully expanded leaves, upper surface: Close to 137A; venation, close to 137A. When opening and fully expanded leaves, lower surface: Close to 137C; venation, close to 137C.

Inflorescence description:

*Appearance and flowering habit*.—Showy zygomorphic flowers arranged on axillary branched racemes; typically two inflorescences per plant; each inflorescence with about 12 to 13 flowers; flowers face outwardly on arching inflorescences supported by upright peduncles; flowers with three petals, two lateral petals and one center petal transformed into a labellum and three sepals.

*Fragrance*.—None detected.

*Time to flower*.—Plants begin flowering about 17 weeks after an inductive cooling period; flowers open about five weeks after flower buds develop.

*Flower longevity*.—Long flowering period, individual flowers maintain good substance for about eleven weeks on the plant; flowers not persistent.

*Inflorescence length* (*lowermost flower to inflorescence apex*).—About 25 cm.

*Inflorescence width*.—About 15 cm by 42 cm.

*Flower buds*.—Height: About 2.5 cm. Diameter: About 1.5 cm. Shape: Ovate. Color: Close to 154C to 154D.

*Flower diameter*.—About 8.5 cm.

*Flower depth*.—About 2.8 cm.

*Petals, quantity and arrangement*.—Three, two lateral petals and one center petal transformed into a labellum.

*Lateral petals*.—Length: About 3.5 cm. Width: About 3.1 cm. Shape: Flabellate. Apex: Rounded. Margin: Entire. Texture and luster, upper and lower surfaces: Smooth, glabrous, velvety; matte. Color: When opening and fully opened, upper surface: Close to 3C; radiating stripes, close to 34A; color does not change with subsequent development. When opening and fully opened, lower surface: Close to 4B; color does not change with subsequent development.

*Labella*.—Appearance: Tri-lobed with two lateral lobes and a central lobe. Length: About 1.9 cm. Width: About 1.6 cm. Shape, lateral lobes: Oblanceolate. Shape, central lobe: Trullate. Apex, lateral lobes: Obtuse. Apex, central lobe: Mucronate with two short, narrow and recurved cirrose tips. Margins, lateral and central lobes: Entire. Texture and luster, upper and lower surfaces: Smooth, glabrous, moderately velvety; matte. Callosities: Located at the base of the labellum and attachment point of the lateral petals; about 5 mm in length, about 4 mm in width and about 3 mm in height. Color: When opening and fully opened, upper surface: Lateral lobes: Close to 14A and 155D; center, close to 81B. Central lobe: Center, close to 34B; towards the base, close to 14A; towards the apex, close to 81B. Callosities: Close to 14A. When opening and fully opened, lower surface: Lateral and central lobes: Close to 14B and 155D; towards the apex, close to 81B.

*Sepals*.—Quantity and arrangement: Three, two lower lateral sepals and one upper dorsal sepal. Length, lateral sepal: About 4.3 cm. Width, lateral sepals: About 2.3 cm. Length, dorsal sepal: About 4 cm. Width, dorsal sepal: About 2.4 cm. Shape, lateral sepals: Ovate. Shape, dorsal sepal: Elliptic. Apex, lateral sepals: Bluntly acute. Apex, dorsal sepal: Obtuse. Base, lateral and dorsal sepals: Acute to obtuse. Margin, lateral and dorsal sepals: Entire. Texture and luster, lateral and dorsal sepals, upper and lower surfaces: Smooth, glabrous, velvety; matte. Color, lateral and dorsal sepals: When opening and fully opened, upper surface: Close to 4B. When opening and fully opened, lower surface: Close to 1A.

*Peduncles*.—Length: About 59 cm. Diameter: About 5.5 mm. Strength: Strong, somewhat flexible. Aspect: Mostly upright. Texture and luster: Smooth, glabrous; matte. Color: Close to 144A.

*Pedicels*.—Length: About 4.3 cm. Diameter: About 3 mm. Strength: Moderately strong. Aspect: About 80° from peduncle axis. Texture and luster: Smooth, glabrous; matte. Color: Close to 145A and 2D.

*Reproductive organs*.—Androecium: Column length: About 1 cm. Column width: About 6 mm. Column color: Close to NN155D. Pollinia quantity: Two. Pollinia diameter (per two pollinia): About 2 mm. Pollinia color: Close to 24A. Gynoecium: Stigma length: About 3 mm. Stigma width: About 3 mm. Stigma shape: Reniform. Stigma color: Close to NN155D. Ovary length: About 1.25 cm. Ovary diameter: About 2 mm. Ovary color: Close to 2D. Seeds and fruits: To date, seed and fruit development have not been observed on plants of the new *Phalaenopsis*.

Pathogen & pest resistance: To date, plants of the new *Phalaenopsis* have not been shown to be resistant to pathogens and pests common to *Phalaenopsis* plants.

Temperature tolerance: Plants of the new *Phalaenopsis* have been observed to tolerate high temperatures of about 40° C. and suitable for USDA Hardiness Zone 10.

It is claimed:

1. A new and distinct *Phalaenopsis* plant named 'MI02648' as illustrated and described.

* * * * *